US010028892B2

(12) United States Patent
MacDonald et al.

(10) Patent No.: US 10,028,892 B2
(45) Date of Patent: Jul. 24, 2018

(54) METHOD AND SYSTEM FOR MONITORING NUTRITIONAL UPTAKE AS A FUNCTION OF HYDROGEN GAS LEVELS

(71) Applicant: Kimberly-Clark Worldwide, Inc., Neenah, WI (US)

(72) Inventors: John Gavin MacDonald, Decatur, GA (US); CholWon Koh, Seoul (KR); InYoung Sa, Gyeong-Gi (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 230 days.

(21) Appl. No.: 14/803,827

(22) Filed: Jul. 20, 2015

(65) Prior Publication Data

US 2015/0320337 A1    Nov. 12, 2015

Related U.S. Application Data

(62) Division of application No. 13/245,412, filed on Sep. 26, 2011, now Pat. No. 9,114,065.

(Continued)

(51) Int. Cl.
*A61J 15/00*    (2006.01)
*A61B 5/00*    (2006.01)
(Continued)

(52) U.S. Cl.
CPC ............... *A61J 15/00* (2013.01); *A61B 5/082* (2013.01); *A61B 5/4866* (2013.01);
(Continued)

(58) Field of Classification Search
CPC .... A61J 15/00; A61J 15/0003; A61J 15/0007; A61J 15/0015; A61J 15/0019;
(Continued)

(56) References Cited

U.S. PATENT DOCUMENTS

| 6,033,367 A | 3/2000 | Goldfield |
| 2005/0008652 A1 | 1/2005 | Lin et al. |

(Continued)

OTHER PUBLICATIONS

Attar, Alain et al., "Antibiotic Efficacy in Small Intestinal Bacterial Overgrowth-Related Chronic Diarrhea: A Crossover, Randomized Trial," Gastroenterology, vol. 117, No. 4, Oct. 1999, pp. 794-797.

(Continued)

*Primary Examiner* — Kami A Bosworth
(74) *Attorney, Agent, or Firm* — Kimberly-Clark Worldwide, Inc.

(57) ABSTRACT

Systems and methods for monitoring nutritional uptake of an individual are disclosed. The method can include monitoring microflora intestinal gas concentration levels associated with a patient and adjusting the volume of nutrient provided by the patient with an artificial feeding device based at least in part on the microflora intestinal gas levels associated with the patient. A microflora intestinal gas sensor can be used to monitor the microflora intestinal gas associated with the patient. The microflora intestinal gas sensor can monitor the microflora intestinal gas in a patient's exhaled breath or in the patient's digestive tract. The microflora intestinal gas sensor be included as part of an enteral feeding system at the distal end or outside end of an enteral feeding tube. Systems and methods for monitoring nutritional uptake of an infant based on microflora intestinal gas levels associated with the infant are also disclosed.

20 Claims, 8 Drawing Sheets

Related U.S. Application Data

(60) Provisional application No. 61/422,730, filed on Dec. 14, 2010.

(51) Int. Cl.
*A61B 5/08* (2006.01)
*A61M 39/08* (2006.01)

(52) U.S. Cl.
CPC .......... *A61B 5/6867* (2013.01); *A61B 5/6871* (2013.01); *A61B 5/6873* (2013.01); *A61J 15/0015* (2013.01); *A61J 15/0084* (2015.05); *A61M 2039/085* (2013.01)

(58) Field of Classification Search
CPC ................ A61J 15/0023; A61J 15/0026; A61J 15/0069; A61J 15/0076; A61J 15/008; A61J 15/0084; A61B 5/6871; A61B 5/6873; A61B 5/4866; A61B 5/083; A61B 5/0833; A61B 5/0836; A61M 2039/085
See application file for complete search history.

(56) References Cited

U.S. PATENT DOCUMENTS

| | | | |
|---|---|---|---|
| 2006/0074335 A1 | 4/2006 | Ben-Oren et al. | |
| 2008/0015523 A1 | 1/2008 | Baker | |
| 2008/0086076 A1* | 4/2008 | Gerber | A61J 15/0003 604/43 |
| 2008/0281194 A1 | 11/2008 | Bush et al. | |
| 2009/0062725 A1 | 3/2009 | Goebel | |
| 2009/0288606 A1 | 11/2009 | Zimmerman | |
| 2010/0030133 A1 | 2/2010 | Elia et al. | |
| 2011/0130650 A1 | 6/2011 | Dayan et al. | |

OTHER PUBLICATIONS

Behall, Kay M. et al., "Breath Hydrogen and Methane Expiration in Men and Women After Oat Extract Consumption," Human Nutrition and Metabolism, The Journal of Nutrition, vol. 128, 1998, pp. 79-84.

Bond, John H. And Michael D. Levitt, "Use of Breath Hydrogen (H2) in the Study of Carbohydrate Absorption," The American Journal of Digestive Diseases, vol. 22, No. 4, Apr. 1977, pp. 379-382.

Homann, H.-H. et al., "Control of Postoperative Enteral Feeding by Hydrogen Breath Test," Clinical Nutrition, vol. 10, Jan. 1, 1991, p. 37, p. 40.

Li, Ding-You et al., "Who Should Request a Breath Hydrogen Test? A Six-Year Feasibility, Sensitivity of Clinical Suspicion and Cost-Effectiveness Analysis," The Journal of Applied Research, vol. 4, No. 2, 2004, pp. 266-270.

Lindberg, Deborah A., "Hydrogen Breath Testing in Adults," Gastroenterology Nursing, vol. 32, No. 1, Jan./Feb. 2009, pp. 19-24.

McNamara, Elizabeth A. et al., "Breath Hydrogen and Methane: Poor Indicators of Apparent Digestion of Soy Fiber," The American Journal of Clinical Nutrition, vol. 43, No. 6, Jun. 1986, pp. 898-902.

Moafi, A. et al., "Oriented Graphitic Carbon Films for Hydrogen Gas Sensors," IEEE Sensors 2010 Conference, pp. 378-381.

Rivera, Ivan F. et. al., "Graphene-Based Ultra-Sensitive Gas Sensors," IEEE Sensors 2010 Conference, 1534-1537.

Shafiei, M. et al., "Pt/Mo03 Nano-flower/Sic Schottky Diode Based Hydrogen Gas Sensor," IEEE Sensors 2010 Conference, pp. 354-357.

Tadesse, K. et al., "Breath Hydrogen (H2) and Methane (CH4) Excretion Patterns in Normal Man and in Clinical Practice," Quarterly Journal of Experimental Physiology, vol. 65, 1980, pp. 85-97.

Varghese, Oomman K. et al., "Hydrogen Sensing Using Titania Nanotubes," Sensors and Actuators, B 93, Elsevier Science, 2003, pp. 338-344.

\* cited by examiner

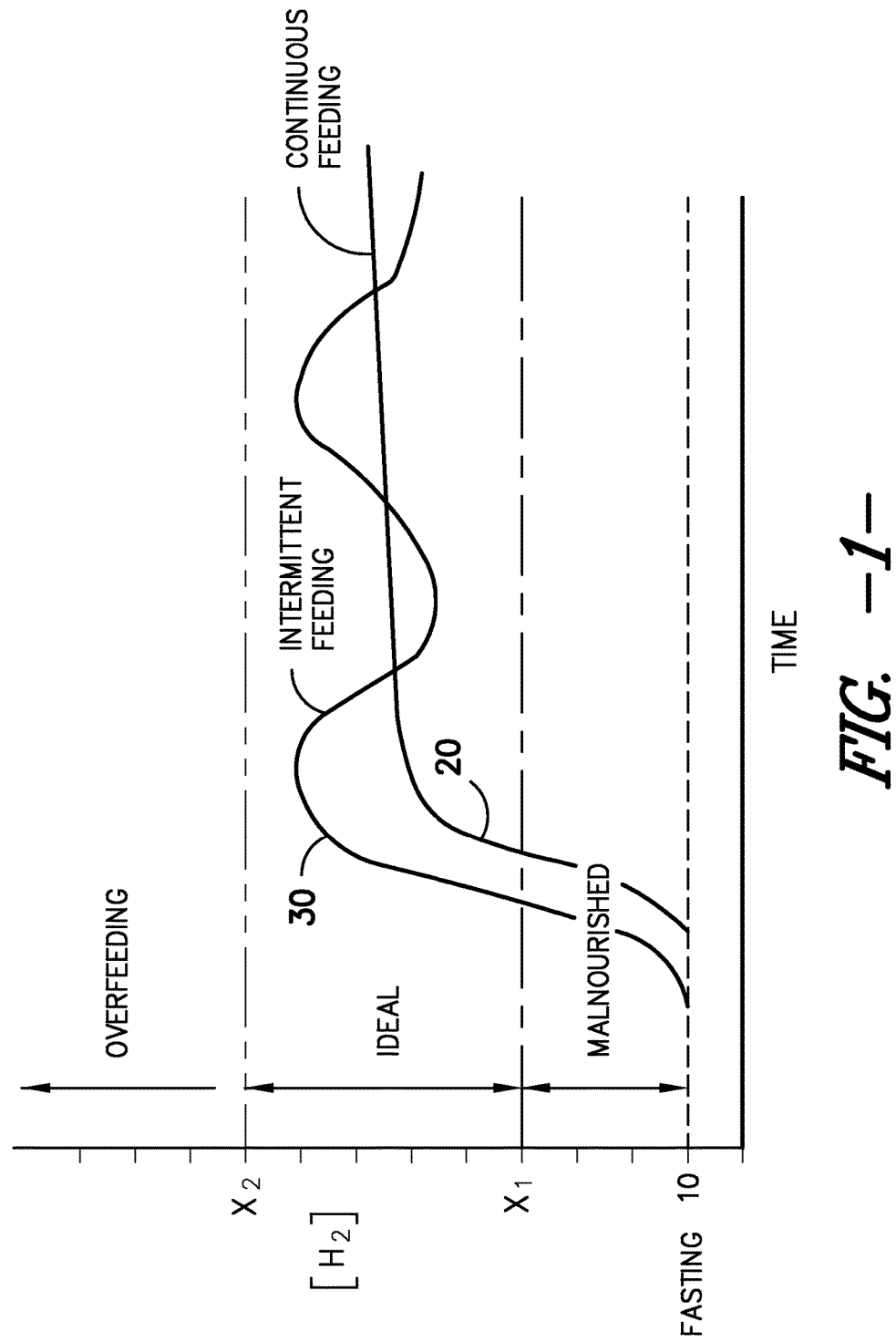
FIG. -1-

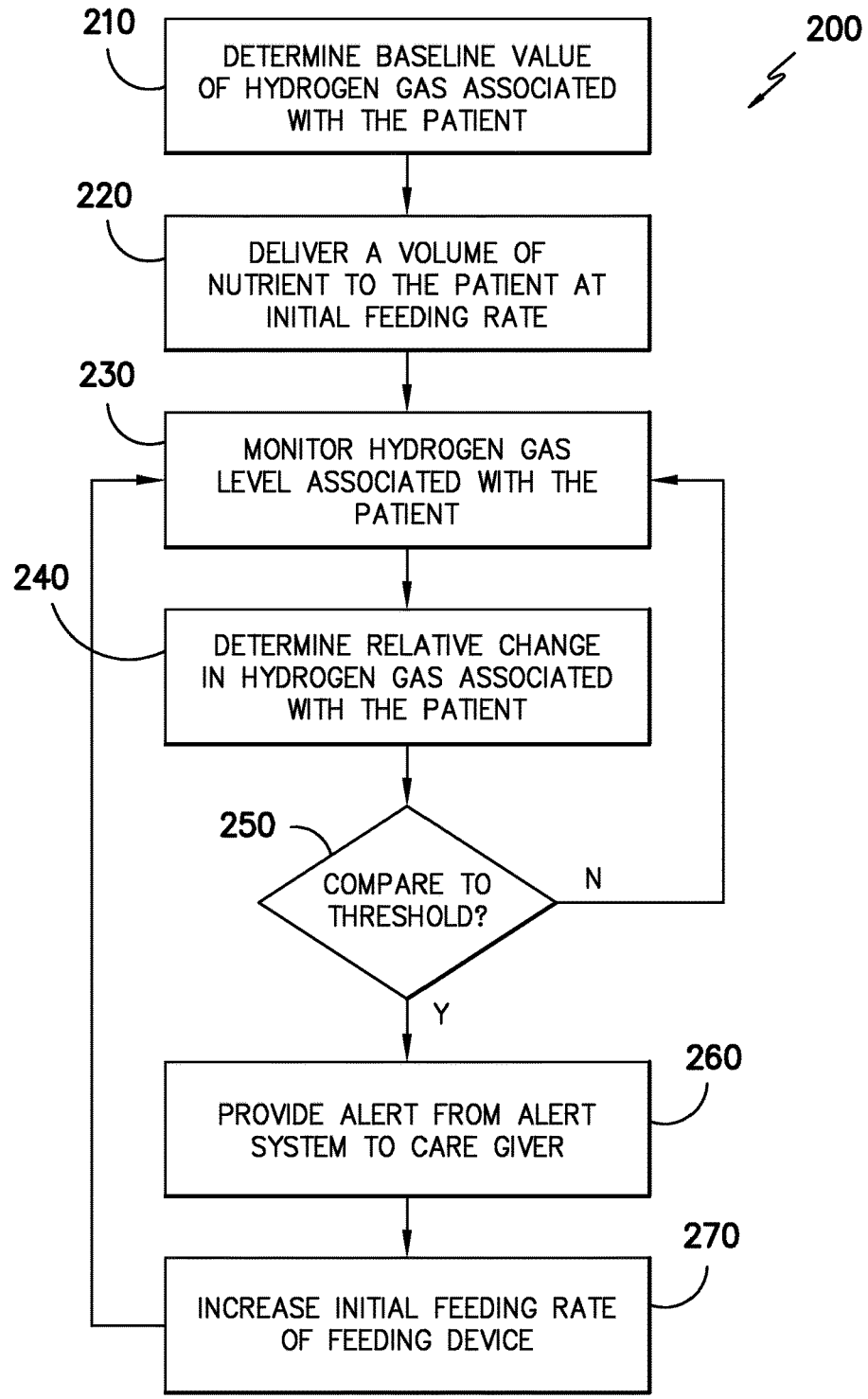
FIG. -2-

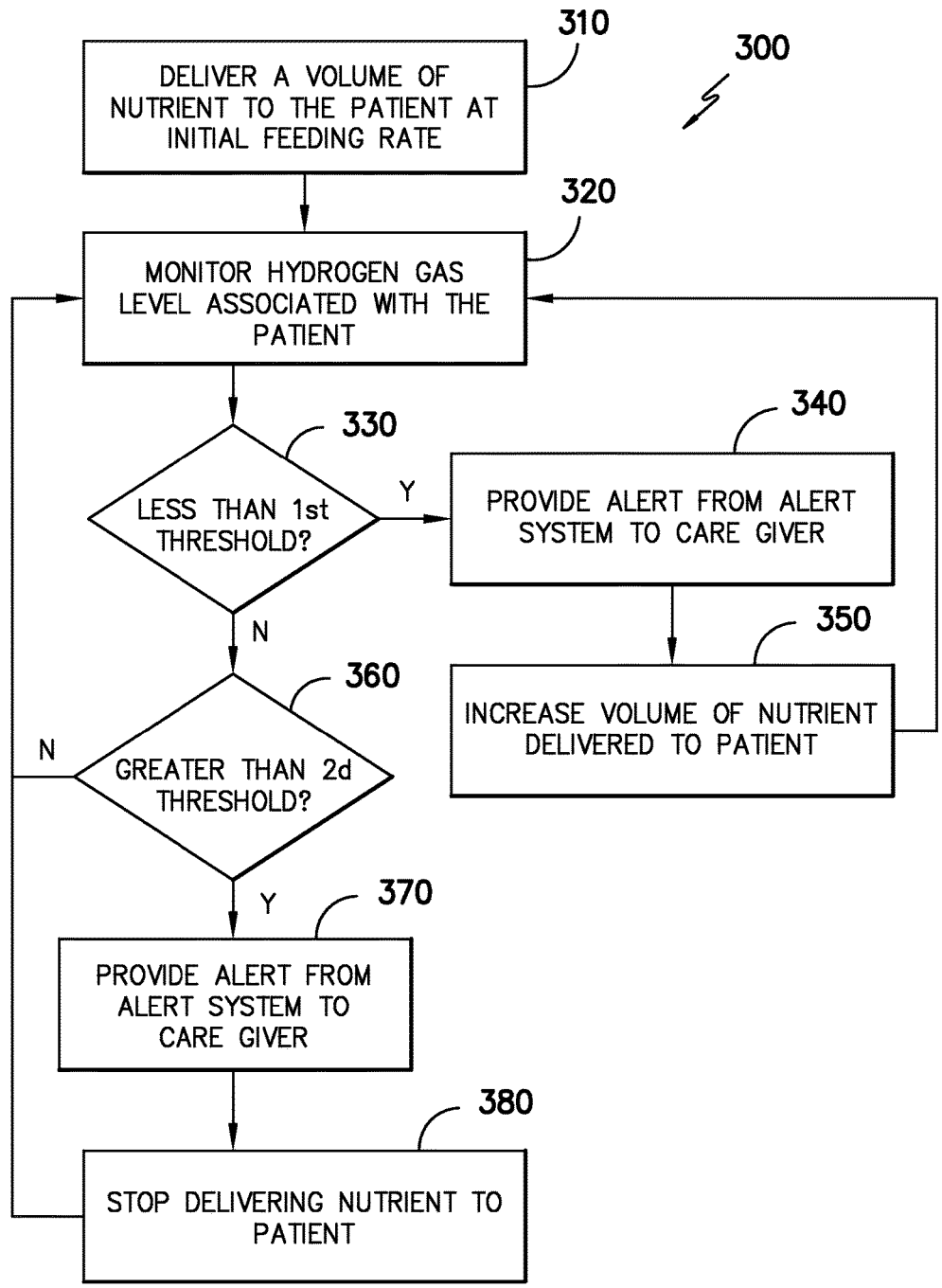
FIG. -3-

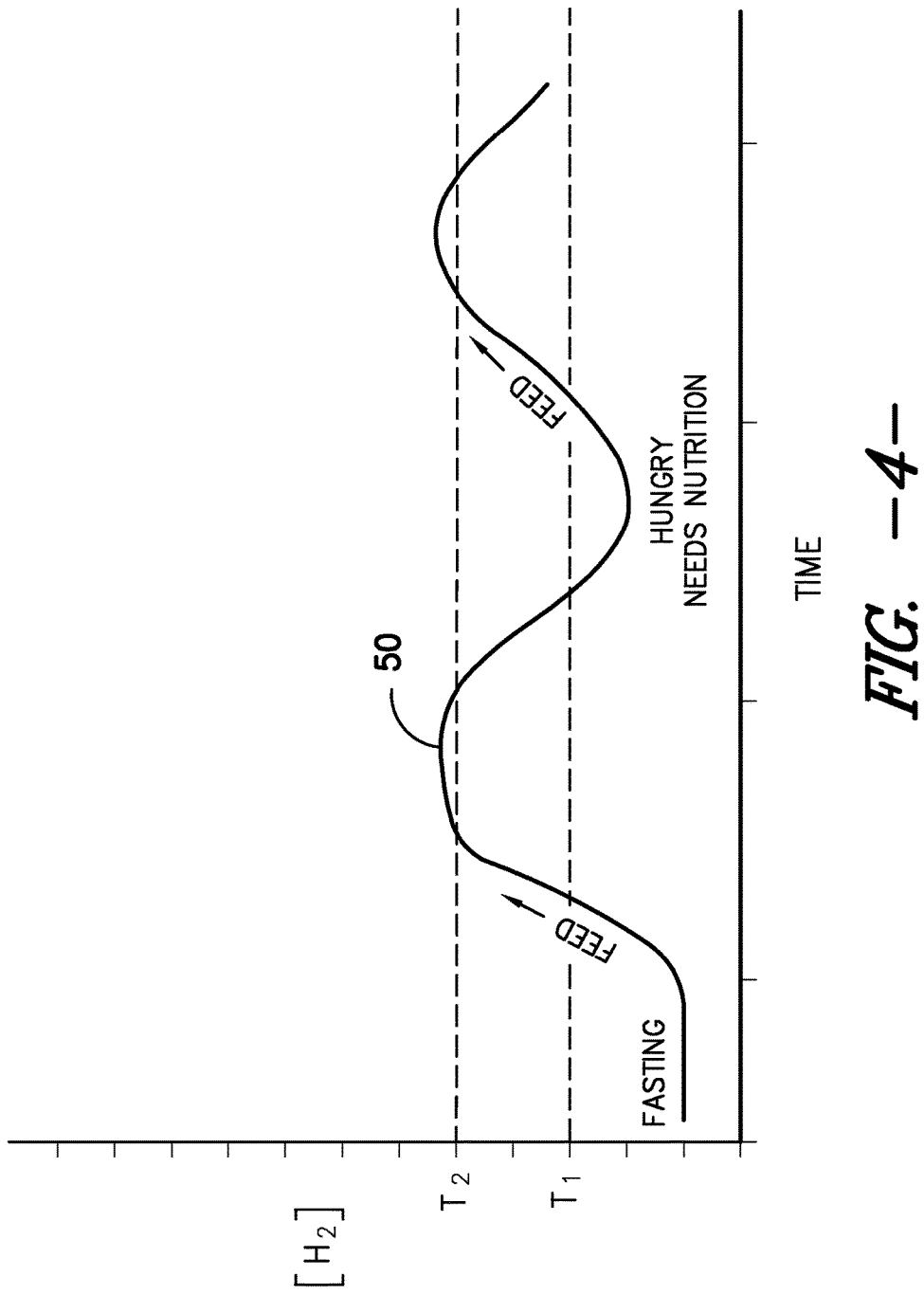
FIG. -4-

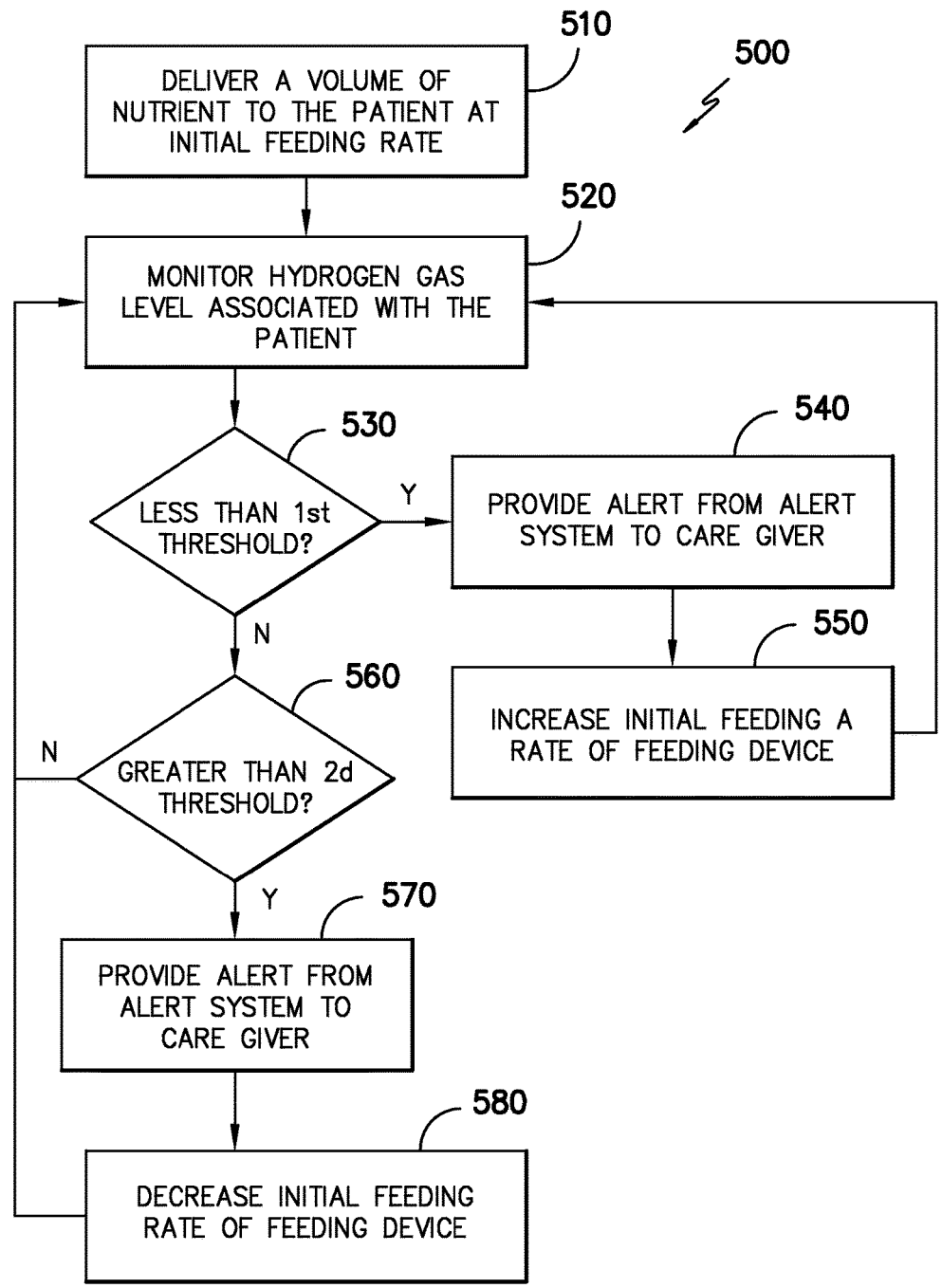
FIG. —5—

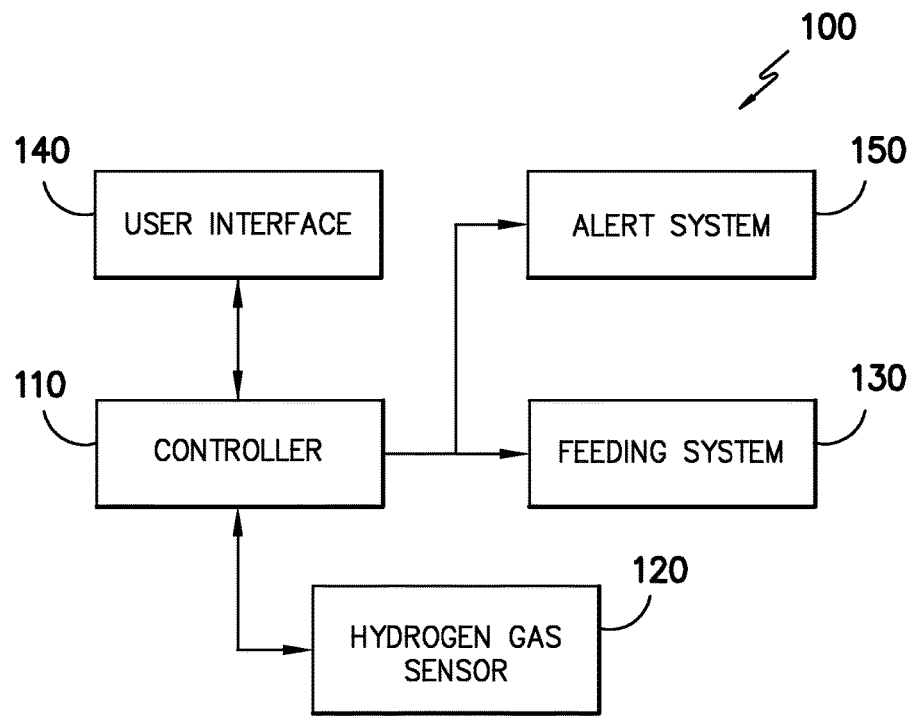
FIG. -6-
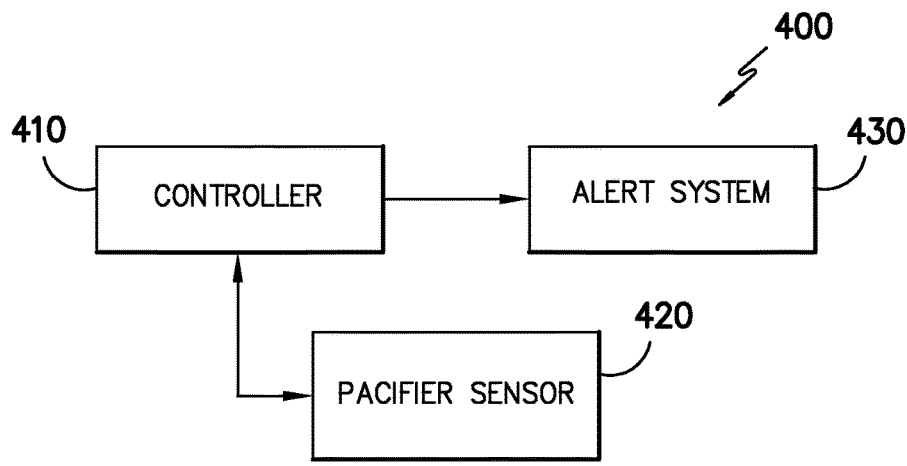
FIG. -9-

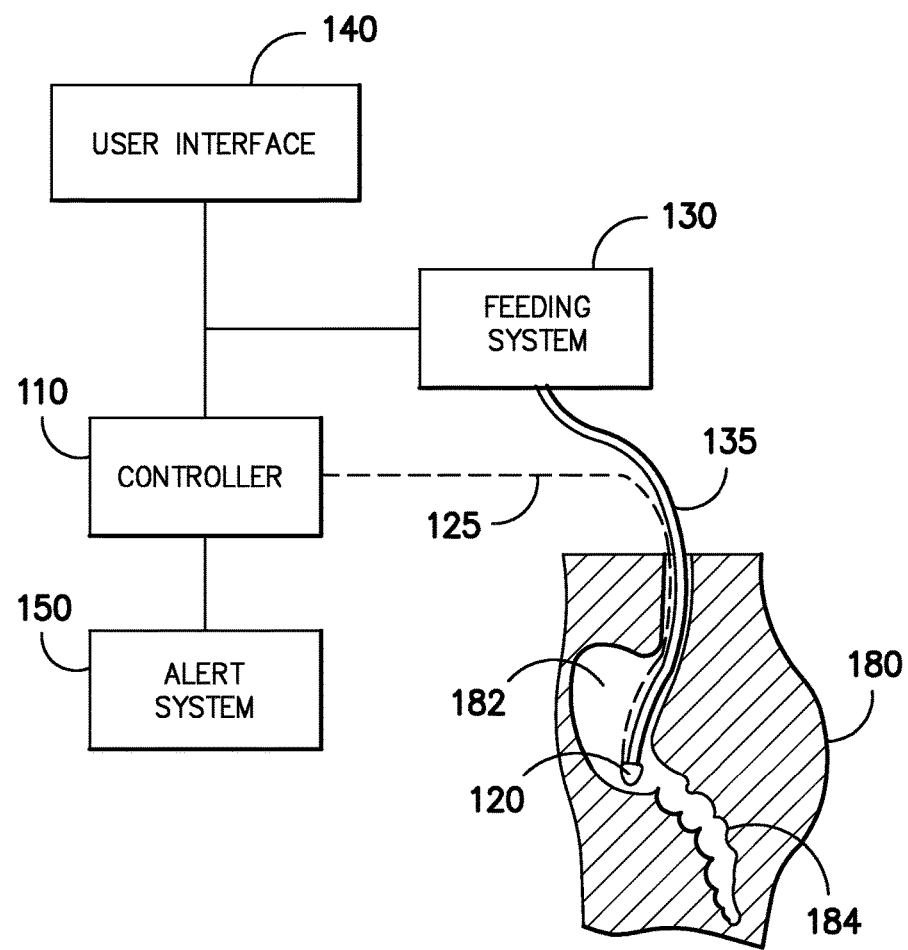
FIG. —7—

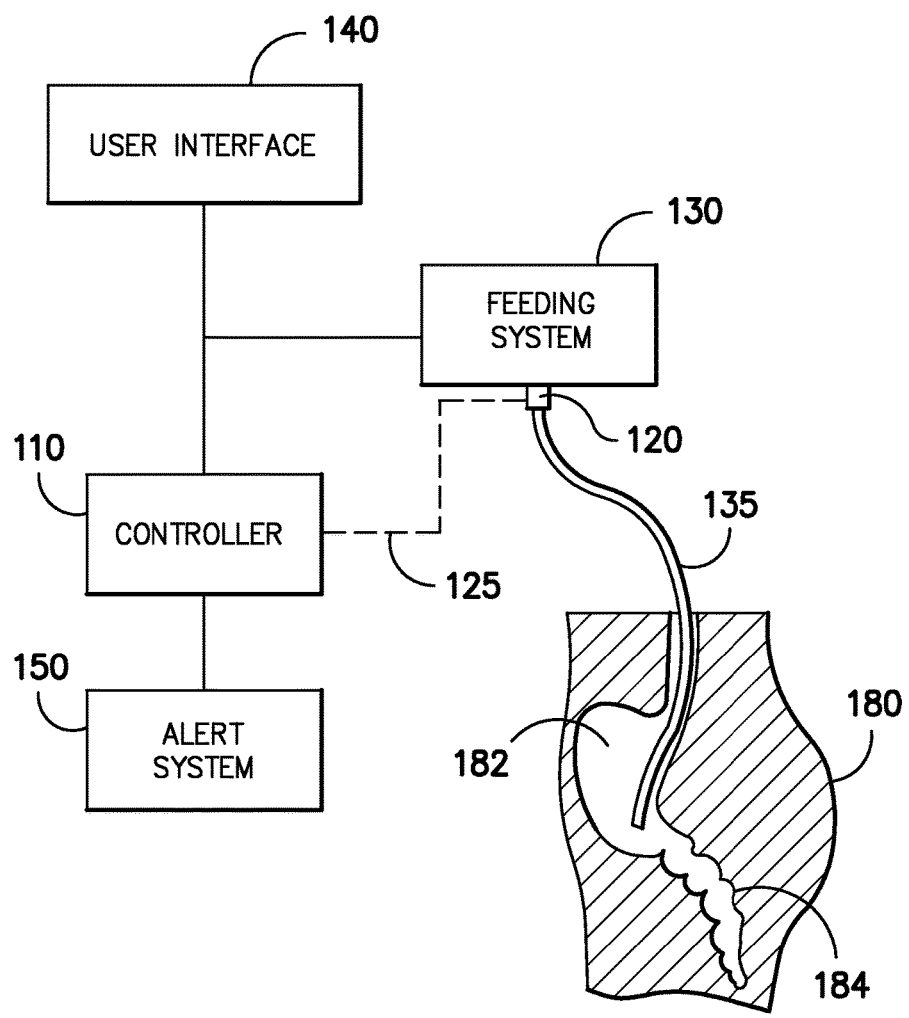
FIG. -8-

METHOD AND SYSTEM FOR MONITORING NUTRITIONAL UPTAKE AS A FUNCTION OF HYDROGEN GAS LEVELS

This application is a divisional of application Ser. No. 13/245,412, now U.S. Pat. No. 9,114,065 granted Aug. 25, 2015, entitled "METHOD AND SYSTEM FOR MONITORING NUTRITIONAL UPTAKE AS A FUNCTION OF MICROFLORA INTESTINAL GAS LEVELS" and filed in the U.S. Patent and Trademark Office on Sep. 26, 2011, and Applicants hereby claim priority from U.S. Provisional Application No. 61/422,730 filed on Dec. 14, 2010. The entirety of the prior applications is hereby incorporated by reference in this application.

FIELD OF THE INVENTION

The present disclosure generally relates to a method and system for monitoring the absorption and digestion of nutrients, and more particularly to a method and system for continuous, real-time monitoring and regulation of feeding of an individual as a function of microflora intestinal gas levels generated in the individual's digestive tract.

BACKGROUND OF THE INVENTION

It is important for many patients, particularly critically ill patients, to receive proper nutrition and to begin feeding as soon as possible. Proper nutrition can lead to shorter recovery times and better mortality and morbidity outcomes. Medical devices that are designed to support artificial feeding in patients include various enteral feeding systems. Enteral feeding systems typically supply nutrition to a patient's digestive tract, specifically the stomach, small intestine or jejunum by inserting a tube down a patient's nose or through the stomach wall. Conversely, parental nutrition is supplied intravenously, circumventing the usual digestion process. Enteral nutrition is typically recommended over parenteral nutrition because, if possible, it is important to use the method closest to natural feeding to keep the gut from shutting down.

Once artificial feeding has begun, it is important to assess how well the patient is tolerating the artificial feeding, as well as to determine if the patient is getting adequate nutrition. Many artificially fed patients can become malnourished due to improper amounts of nutrient being provided to the patient. This problem is enhanced in situations where the care giver slows down the feeding rate to prevent vomiting and diarrhea.

Current clinical methods used to monitor the nutritional uptake and status of artificially fed patients include daily blood tests to determine, for instance, albumin, prealbumin, electrolyte, creatine, and blood sugar levels, and 72 hour fecal fat content tests. In addition, bowel movements, urine assessment, and, if the patient is awake, strength and alertness can be observed. These methods involve long time gaps and do not offer real-time information concerning the patient's nutritional uptake to the care giver.

Thus, there is a need for a real-time nutritional uptake monitoring system and method to provide information that a patient is receiving sufficient nutrition. A system and method for informing a care giver whether too little, an ideal amount, or too much is being fed to the patient would be particularly useful.

Monitoring nutritional uptake can also be important in the specific feeding of infants. Parents and other care takers can have a more difficult time determining when an infant child is hungry or is need of feeding. In addition, weight gain and overall health status is the primary method of assessing proper nutrient delivery for breast feed infants. Thus, there is similarly a need for a specific system and method of real-time nutritional uptake monitoring to provide information that an infant is receiving sufficient nutrition.

SUMMARY OF THE INVENTION

The present invention relates to a method of monitoring artificial feeding of a patient, comprising: delivering a volume of nutrient to the patient with a feeding device at an initial feeding rate; monitoring an amount of microflora intestinal gas associated with the patient with a gas sensor able to detect microflora intestinal gas; and adjusting the volume of nutrient delivered to the patient based at least in part on the amount of microflora intestinal gas associated with the patient.

Additionally, the present invention relates to a system for monitoring artificial feeding of a patient, the system comprising: a feeding device configured to deliver a volume of nutrient to a patient at an initial feeding rate; a gas sensor able to detect microflora intestinal gas configured to monitor an amount of microflora intestinal gas associated with the patient; and a controller configured to adjust the volume of nutrient delivered to the patient based at least in part on the amount of microflora intestinal gas associated with the patient.

The present invention also relates to a system for monitoring nutritional uptake of an infant, the system comprising: a gas sensor able to detect microflora intestinal gas sensor configured to monitor an amount of microflora intestinal gas associated with the exhaled breath of the infant; an electronic circuit coupled to said gas sensor, the electronic circuit configured to provide an alert to a care giver based at least in part on the amount of microflora intestinal gas detected by said gas sensor.

Finally, the present invention also relates to a method of monitoring nutritional uptake of an infant, the method comprising: monitoring an amount of microflora intestinal gas level in the exhaled breath of the infant using a gas sensor able to detect microflora intestinal gas; comparing the amount of microflora intestinal gas with a threshold value; providing an alert if the amount of microflora intestinal gas is less than the threshold value.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which:

FIG. 1 provides a graphical representation of hydrogen concentration versus feeding over time;

FIG. 2 provides a flow chart of an exemplary method according to an exemplary embodiment of the present disclosure;

FIG. 3 provides a flow chart of an exemplary method for intermittent feeding according to an exemplary embodiment of the present disclosure;

FIG. 4 provides a graphical representation of hydrogen concentration versus feeding over time;

FIG. 5 provides a flow chart of an exemplary method for continuous feeding according to an exemplary embodiment of the present disclosure;

FIG. 6 provides a block diagram of an exemplary system for monitoring nutritional uptake of an artificially fed patient according to an exemplary embodiment of the present disclosure;

FIG. 7 depicts an exemplary system for monitoring nutritional uptake of an artificially fed patient according to an exemplary embodiment of the present disclosure;

FIG. 8 depicts an exemplary system for monitoring nutritional uptake of an artificially fed patient according to an exemplary embodiment of the present disclosure; and FIG. 9 depicts a block diagram of an exemplary system for monitoring nutritional uptake of an infant according to an exemplary embodiment of the present disclosure.

Repeat use of reference characters in the present specification and drawings is intended to represent the same or analogous features or elements of the present invention. It is also understood that while hydrogen gas is exemplified by way of the figures, the present invention is not limited to only the concentrations of hydrogen gas but can account for all concentrations of microflora intestinal gas levels.

DETAILED DESCRIPTION OF THE INVENTION

While the specification concludes with the claims particularly pointing out and distinctly claiming the invention, it is believed that the present invention will be better understood from the following description.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein. Except where specific examples of actual measured values are presented, numerical values referred to herein should be considered to be qualified by the word "about".

As used herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

As used herein, the term "microflora intestinal gas" refers to gases such as carbon dioxide, oxygen, nitrogen, hydrogen, ammonia, acetone and methane produced by the microflora present in the intestine as the microflora break down carbohydrates for absorption through the intestine wall. Since a patient may produce any of these gases, the method of the present invention directs the monitoring for artificial feeding towards the concentrations of gases delivered by the intestinal walls.

One exemplary embodiment of the present disclosure is directed to a method of monitoring artificial feeding of a patient. The method includes delivering a volume of nutrient to the patient with a feeding device, such as an enteral feeding device, at an initial feeding rate. The method further includes monitoring an amount of microflora intestinal gas associated with the patient with a gas sensor able to detect such microflora intestinal gases; and adjusting the volume of nutrient delivered to the patient based at least in part on the amount of microflora intestinal gas associated with the patient. For instance, in a particular embodiment, adjusting the volume of nutrient delivered to the patient comprises adjusting the initial feeding rate of the feeding device based at least in part on the amount of microflora intestinal gas associated with the patient.

In a particular aspect of this exemplary embodiment, the feeding device can be coupled to a control loop configured to regulate the volume of nutrient delivered by the feeding device based at least in part on the amount of microflora intestinal gas detected by the gas sensor able to detect microflora intestinal gas.

In another particular aspect of this exemplary embodiment, the method includes monitoring an amount of microflora intestinal gas associated with the patient before delivering a volume of nutrient to the patient to determine a baseline value of microflora intestinal gas for the patient. The method can further include determining the relative change in microflora intestinal gas associated with the patient from the baseline value after delivering a volume of nutrient to the patient and adjusting the volume of nutrient delivered to the patient based at least in part on the relative change in microflora intestinal gas from the baseline value.

While the majority of people produce hydrogen gas when digesting food, there are a small percentage of people who do not, i.e. the "non-hydrogen producers". This is due, in part, to the microbial make up of their gut flora. However, all people produce and exhale methane gas. A system that monitors the concentration levels of methane exhaled, or more preferably both hydrogen and methane gases exhaled, would allow a universal monitoring device that could be used for all people. The breath analysis unit as shown in FIG. 2 is a good example of an embodiment that measure both hydrogen and methane breath gases simultaneously. Based on the levels of methane gas present, one could determine if a person was receiving enough nutrition, receiving too much nutrition or receiving just the right amount of nutrition.

For example, normal methane gas levels before eating (fasting/malnourished) would exhibit a methane range of from about 5 to about 15 ppm. After eating, a normal methane range would be from about 20 to about 60 ppm. If a person is overfed, (danger of vomiting or diarrhea or pulmonary aspiration) methane levels would be from about 60 ppm or above. For people who produce both hydrogen and methane, the nutritional digestion process could also be monitored via the sum of both gases which shows a linear dose-effect relationship "Breath hydrogen and methane expiration in men and women after oat extract consumption," Behall, K. M., Scholfield, D. J., van der Sluijs, A. M. C., Hallfrisch, J., 128 J. Nutrition 79-84 (1998). In still another particular aspect of this exemplary embodiment, delivering a volume of nutrient to the patient with the feeding device includes intermittently delivering the nutrient to the patient. Adjusting the volume of nutrient delivered to the patient can include providing nutrient to the patient with the feeding device when the amount of microflora intestinal gas associated with the patient is less than a first threshold value. When detecting levels of hydrogen gas, for example, nutrients can be provided to a patient intermittently when the levels are less than the threshold value in the range of about 5 ppm to about 25 ppm, such as about 10 ppm to about 20 ppm, such as about 20 ppm, or any other hydrogen gas concentration therebetween) and stopping delivery of nutrient to the patient when the amount of hydrogen gas associated with the patient is greater than a second threshold value (such as greater than a threshold value in the range of about 65 ppm to about 85 ppm, such as about 75 ppm to about 80 ppm, such as about 80 ppm, or any other hydrogen gas concentration therebetween). When detecting levels of methane gas, for example, nutrients can be provided to a patient intermittently when the levels are less than a first threshold value (such as less than threshold value in the range of about 3 ppm to about 20 ppm, such as about 5 ppm to about 15 ppm, such as about 15 ppm, or any other methane gas concentration therebetween) and stopping delivery of nutrient to the patient when the amount of hydrogen gas associated with the patient is greater than a second threshold value (such as greater than a threshold value in the range of about 55 ppm to about 65 ppm, such as about 60 ppm, or any other hydrogen gas concentration therebetween).

In still a further aspect of this exemplary embodiment, delivering a volume of nutrient to the patient with the feeding device includes continuously delivering the nutrient to the patient. Adjusting the volume of nutrient delivered to the patient can include increasing the initial feeding rate if the detected amount of microflora intestinal gas is less than a first threshold value. When detecting levels of hydrogen gas, for example, nutrients can be provided to a patient continuously when the levels are in the range of about 5 ppm to about 25 ppm, such as about 10 ppm to about 20 ppm, such as about 20 ppm, or any other hydrogen gas concentration therebetween), maintaining the initial feeding rate substantially constant if the detected amount of hydrogen is greater than the first threshold value and less than a second threshold value (such as a threshold value in the range of about 65 ppm to about 85 ppm, such as about 75 ppm to about 80 ppm, such as about 80 ppm, or any other hydrogen gas concentration therebetween), and decreasing the initial feeding rate if the detected amount of hydrogen gas is greater than the second threshold value. When detecting levels of methane gas, for example, nutrients can be provided to a patient continuously when the levels are less than a first threshold value (such as a threshold value in the range of about 3 ppm to about 20 ppm, such as about 5 ppm to about 15 ppm, such as about 15 ppm, or any other methane gas concentration therebetween), maintaining the initial feeding rate substantially constant if the detected amount of hydrogen/methane is greater than the first threshold value and less than a second threshold value (such as a threshold value in the range of about 55 ppm to about 65 ppm, such as about 60 ppm, or any other methane gas concentration therebetween), and decreasing the initial feeding rate if the detected amount of methane gas is greater than the second threshold value.

In further particular aspects of this exemplary embodiment, monitoring an amount of microflora intestinal gas associated with the patient can include monitoring a concentration of microflora intestinal gas in the patient's breath, such as monitoring a concentration of microflora intestinal gas in the exhaled breath of the patient. Alternatively, monitoring an amount of microflora intestinal gas associated with the patient can include monitoring a concentration of microflora intestinal gas in the patient's digestive tract, such as in the patient's stomach or small intestine.

Another exemplary embodiment of the present disclosure is directed to a system for monitoring artificial feeding of a patient. The system includes a feeding device, such as an enteral feeding device, configured to deliver nutrient to a patient at an initial feeding rate; a gas sensor able to detect microflora intestinal gas configured to monitor an amount of microflora intestinal gas associated with the patient; and a controller configured to adjust the volume of nutrient delivered to the patient based at least in part on the amount of microflora intestinal gas associated with the patient.

In a particular aspect of this exemplary embodiment, the microflora intestinal gas sensor includes a sensor configured to monitor the exhaled breath of the patient. For instance, the sensor can be a stand-alone breathalyzer sensor device or can be included on a ventilator tube used by the patient.

In another particular aspect of this exemplary embodiment, the feeding device includes an enteral feeding tube having a distal end inserted into the digestive tract of the patient and an outside end coupled to a nutrient source. In one implementation, the microflora intestinal gas sensor can be located at the distal end of the feeding tube such that the microflora intestinal gas sensor monitors an amount of microflora intestinal gas in the stomach of the patient or in the small intestine of the patent. In another implementation, the microflora intestinal gas sensor can be located at or near the outside end of the enteral feeding tube.

In still another particular aspect of this exemplary embodiment, the system can include an alert system configured to alert a care giver based at least in part on the amount of microflora intestinal gas detected by the microflora intestinal gas sensor. For instance, the alert system can provide an alert to a care giver if the amount of microflora intestinal gas associated with the patient is less than or greater than a particular threshold value. The alert can be an audible, visual, vibratory, wireless, or other suitable alert.

A further exemplary embodiment of the present disclosure is directed to a system for specifically monitoring nutritional uptake of an infant. The system can include a microflora intestinal gas sensor configured to monitor an amount of microflora intestinal gas associated with the exhaled breath of the infant and an electronic circuit coupled to the microflora intestinal sensor. The electronic circuit can be configured to provide an alert, such as an audible, visual, vibratory, or wireless alert, to a care giver based at least in part on the amount of microflora intestinal gas detected by the microflora intestinal gas sensor. For instance, the electronic circuit can be configured to provide an alert when the amount of microflora intestinal gas detected by the microflora intestinal gas sensor is less than a threshold value. In a particular implementation of this exemplary embodiment, the microflora intestinal gas sensor can be incorporated into or can be located on an oral infant device such as a pacifier, bottle or the like device used by the infant. Due to ease, the present invention prefers the use of a pacifier. However, the ease of use for the present invention, does not limit the present method to a pacifier when an infant is involved. Other devices include, but are also not limited to, bottles, thermometers, teething rings, and the like that may be used to detect the amount of microflora intestinal gases of an infant.

Still a further exemplary embodiment of the present disclosure is directed to a method for monitoring nutritional uptake for an infant. The method includes monitoring an amount of microflora intestinal gas level in the exhaled breath of the infant using a microflora intestinal sensor; comparing the amount of microflora intestinal gas with a threshold value; and providing an alert if the amount of microflora intestinal gas is less than the threshold value.

The present disclosure is generally directed to methods and systems for real-time monitoring of nutritional uptake as a function of microflora intestinal gas generated in the digestive tract. While the present disclosure generally discusses the monitoring and regulation of nutritional uptake in artificially fed patients, those of ordinary skill in the art, using the disclosures provided herein, should understand that the methods and systems of the present disclosure are applicable to any situation where the nutritional uptake of a person needs to be monitored. For instance, the systems and methods of the present disclosure can be used to monitor nutritional uptake of an infant.

A connection exists between microflora intestinal gas concentration in the small intestine, stomach, and breath and the absorption of nutrients in the human body. "Who should request a breath hydrogen test" Li, D-Y, Barnes, T., Thompson, R. E., Cuffari, C., Journal of Applied Research, 4(2), 266 (2004); "Hydrogen breath testing in adults," Lindberg, D. A., Gastroenterology Nursing, 32(1), 19-24 (2009); "Antibiotic efficacy in small intestinal bacterial overgrowth." Attar, A., Flourie, B., Rambaud, J-C., Frachisseur, C., Ruszniewski, P., Bouhnik, Y., Gastroenterology, 117(4), 794-797 (1999).

Hydrogen gas and methane gas is produced by the microflora present in the intestine as the microflora break down carbohydrates for absorption through the intestine wall. In addition, it has been shown that an increase in the concentration of hydrogen gas correlates to an increase in blood glucose when being fed a specific dose of carbohydrate. "Breath hydrogen and methane excretion patterns in normal man and in clinical practice," Tadesse, K., Smith, D., Eastwood, M. A., 65 Quarterly Journal of Experimental Physiology, 85-97 (1980); "Use of breath hydrogen in the study of carbohydrate absorption," Bond, J. H., Levitt, M. D., Digestive Diseases, 22(4), 379-382 (1997); "Breath hydrogen and methane expiration in men and women after oat extract consumption," Behall, K. M., Scholfield, D. J., van der Sluijs, A. M. C., Hallfrisch, J., 128 J. Nutrition 79-84 (1998). Because of the correlation between microflora intestinal gas concentration and nutritional uptake, target ranges for microflora intestinal gas in the breath and/or digestive tract can be developed to inform a care giver that a patient is malnourished, being fed at the correct rate, or being fed too much and is in danger of vomiting or diarrhea.

A microflora intestinal gas sensor can be used to monitor the concentration of microflora intestinal gas in a patient's exhaled breath or in the patient's digestive tract. In fact, the present invention utilizes a microflora intestinal gas sensor for monitoring a concentration of microflora intestinal gas from areas that may expel microflora intestinal gas from the body. Such areas may be selected from the patient's breath, the patient's digestive tract, or the combinations thereof. Signals received from the microflora intestinal gas sensor can be compared to threshold values to alert a caregiver that the volume of nutrient being provided to the patient needs to be increased, decreased, or maintained substantially constant. In addition, the signals received from the microflora intestinal sensor can be used as part of a feedback control loop to control a feeding system to increase, decrease, or maintain the feeding rate as appropriate. In this manner, the methods and systems of the present disclosure can be used to provide real-time monitoring and regulation of nutritional uptake in, for instance, artificially fed patients, infants, and other suitable individuals.

Microflora Intestinal Gas Sensors

Gas sensors suitable for providing real-time monitoring and regulation of nutritional uptake of the present invention may be any device suitable for detecting expelled microflora intestinal gases. Without being limited by theory, sensors such as the Optical nose (O-nose), developed by Pranalytica, for example is capable of measuring gases such as NO, NO2, NH3, SO2 and CH4. Accordingly, this optical device could be designed for the detection microflora intestinal gas concentrations from the expired breath. Additionally, City Technology offers various industrial as well as medical grade hydrogen sensors that may also be suitable to carry out the present invention. Further, a sensors system has been developed by Costello et al to monitor various VoCs in exhaled breath as shown in FIG. 6. The sensors are based on electrochemical gas sensors such as hydrogen, CO, H2S, ethanol, and ammonia. Finally, Argonne National Lab has developed palladium nanobeads for a fast as well as sensitive hydrogen detection particularly for fuel cell applications. This nanosensor shows high selectivity and could detect H2 in presence of oxygen, humidity and other gases. These and other similarly functioning devices capable of detecting the microflora intestinal gas concentration levels may be used and/or designed to carry out the methods of the present invention.

Microflora present in the intestine is able to produce gases such as carbon dioxide, oxygen, nitrogen, hydrogen, ammonia, acetone and methane as the microflora break down carbohydrates for absorption through the intestine wall. Methods of the present invention are able to detect the levels of such gases in order to aid in monitoring nutritional uptake. Specifically, methods of the present invention may comprise monitoring the levels of microflora intestinal gases produced by a patient. Methods of the present invention may further comprise the monitoring of microflora intestinal concentrations. Illustrations included herein, show, for example, concentrations of hydrogen gas. Again, it is understood that while the illustrations of the present specification show hydrogen gas concentration, the same figures could be depicted for all microflora intestinal gas concentrations.

Exemplary regulation of nutritional uptake based on hydrogen gas concentration is illustrated in FIG. 1. FIG. 1 depicts two hydrogen concentration thresholds X1 and X2. Thresholds X1 and X2 are determined such that hydrogen gas concentrations of less than threshold X1 indicate that the patient is malnourished and hydrogen gas concentrations of greater than threshold X2 indicate that the patient is being overfed. Hydrogen gas concentrations greater than X1 and less than X2 indicate that the patient is receiving an ideal amount of nutrition.

FIG. 1 illustrates two hypothetical curves 20, 30 of hydrogen gas concentration over time. Curve 20 is associated with continuous artificial feeding of a patient over time. Curve 30 is associated with intermittent artificial feeding of a patient over time. As illustrated in FIG. 1, with proper monitoring provided by the systems and methods of the present disclosure, the hydrogen gas concentration associated with curves 20 and 30 can be maintained between X1 and X2 such that the patient is receiving an ideal amount of nutrition. Should the curves 20, 30 ever fall below threshold X1 or exceed threshold X2, the systems and methods of the present disclosure could alert a care giver that the patient is not receiving the proper amount of nutrition. In addition, the volume of nutrient provided to the patient can be adjusted such that the proper amount of nutrient is provided to the patient.

For example, FIG. 2 illustrates an exemplary method 200 for monitoring nutritional uptake based on hydrogen gas concentration according to an exemplary embodiment of the present disclosure. The method 200 can be used to calibrate an artificial feeding system or to determine whether the initial feeding rate of nutrient provided by the artificial feeding system is sufficient to provide adequate nutrition to the patient.

As shown in FIG. 2 at 210, a baseline value of hydrogen gas associated with the patient is determined before any nutrient is delivered to the patient by the artificial feeding system. The baseline value of hydrogen gas can be determined using a hydrogen gas sensor as will be discussed in more detail below.

At 220, a volume of nutrient is delivered to the patient with the artificial feeding system at an initial feeding rate. As used herein, the term feeding rate is intended to refer to the rate nutrient is delivered to the patient with an artificial feeding system.

At 230, the hydrogen gas concentration associated with the patient is again monitored with the hydrogen gas sensor. Step 230 can be performed after sufficient passage of time, such as 15 minutes, to allow for adequate absorption of nutrients into the patient. At 240, the relative change in hydrogen gas concentration from the baseline value is determined, for instance, by subtracting the baseline value of hydrogen gas from the monitored hydrogen gas concentration.

At 250, the relative change in hydrogen gas concentration is compared to a threshold value. For instance, in a particular embodiment, the relative change in hydrogen gas can be compared to a first threshold value. The first threshold value can be set such that a relative change in hydrogen gas that falls below the first threshold value indicates that the patient is not receiving adequate nutrition. If the relative change in hydrogen gas concentration exceeds the first threshold value, the artificial feeding system is providing sufficient nutrition to the patient and no increase to the volume of nutrient being delivered to the patient is necessary.

As shown at 260, if the relative change in hydrogen gas concentration is less than the first threshold value, the patient is not receiving an adequate amount of nutrients from the feeding system and an alert, such as an audible, visual, vibratory, or wireless alert, is provided to a the care giver indicating to the care giver that the patient is not receiving adequate nutrition. At 270, the volume of nutrient delivered to the patient is increased, for instance, by increasing the initial feeding rate of the feeding device. The volume of nutrient can be manually increased by the care giver upon receiving the alert or can be increased automatically by a control loop that adjusts the feeding rate of the artificial feeding system based on the hydrogen gas levels associated with the patient. In this way, the method 200 adjusts the volume of nutrient delivered to the patient based on the amount of hydrogen gas associated with the patient and provides for regulation of the amount of nutrient delivered to the patient based on hydrogen gas concentration levels.

In a variation or in addition to the exemplary method illustrated in FIG. 2, the relative change in hydrogen gas can be compared to a second threshold value. The second threshold value can be set such that a relative change in hydrogen gas that exceeds the second threshold value indicates that the patient is receiving too much nutrition. If the relative change in hydrogen gas concentration is greater than the second threshold value, the patient is receiving too much nutrient and is in danger of vomiting and/or diarrhea. An alert, such as an audible, visual, vibratory, or wireless alert, can be provided to a the care giver indicating to the care giver that the patient is receiving too much nutrition. The volume of nutrient delivered to the patient can then be decreased, for instance, by decreasing the initial feeding rate of the feeding device.

FIG. 3 illustrates another exemplary method 300 associated with monitoring nutritional uptake based on hydrogen gas concentration associated with a patient. The method 300 can be used to monitor and regulate the intermittent feeding of the patient with an artificial feeding system. In particular, the method 300 can be used to determine the start and stop times for intermittent feeding of the patient with the artificial feeding system.

At 310, a volume of nutrient is delivered to the patient at an initial feeding rate. The volume of nutrient can be delivered by an enteral feeding system. At 320, the hydrogen gas concentration associated with the patient is monitored using a hydrogen gas sensor. For instance, a hydrogen gas sensor can be used to monitor the amount of hydrogen gas in the patient's exhaled breath or in the patient's digestive tract.

At 330, the hydrogen gas concentration is compared to a first threshold value, such as first threshold value T1 illustrated in FIG. 4. The first threshold value can be, for instance, in the range of about 5 ppm to about 25 ppm, such as about 10 ppm to about 20 ppm, such as about 20 ppm, or any other hydrogen gas concentration therebetween. If the hydrogen gas concentration is less than first threshold value, the patient is in need of additional nutrition. Accordingly, referring back to FIG. 3, an alert can be provided to the care giver from an alert system as shown at 340. In addition, the volume of nutrient delivered to the patient from the feeding system can be increased as shown 350 to accommodate the patient's need for additional nutrition. A care giver can manually increase the volume of nutrient delivered to the patient, or a control loop can automatically adjust feeding system parameters to increase the volume of nutrition delivered to the patient. After increasing the volume of nutrient delivered to the patient, the method 300 returns to 320 and continuously monitors the hydrogen gas associated with the patient to determine if the patient is receiving too little, an ideal amount, or too much nutrition.

At 360, the hydrogen gas concentration is compared to a second threshold, such as threshold T2 illustrated in FIG. 4. Second threshold, for instance, can be in the range of about 65 ppm to about 85 ppm, such as about 75 ppm to about 80 ppm, such as about 80 ppm, or any other hydrogen gas concentration therebetween. If the hydrogen gas concentration is less than the second threshold value, but greater than the first threshold, the patient is receiving an ideal an amount of nutrition. Thus, no adjustments to the feeding system are necessary and the method 300 continues to monitor hydrogen gas concentrations associated with the patient.

If the hydrogen gas concentration exceeds the second threshold value, the patient is receiving too much nutrition and is in danger of vomiting or diarrhea. An alert can be provided to the care giver from an alert system as shown at 370. To prevent overfeeding, the method 300 will stop delivering nutrient to the patient and will continue to monitor hydrogen gas associated with the patient as shown at 380. When the hydrogen gas levels fall below the first threshold, the method 300 will begin delivering nutrient to the patient again to prevent the patient from becoming malnourished.

FIG. 4 provides a graphical illustrated of hydrogen gas concentration levels associated with a patient that is being intermittently fed according to the method 300 of FIG. 300. As illustrated, the hydrogen gas level associated with the patient increases past threshold T1 as the artificial feeding system delivers a volume of nutrient to the patient. As the patient is fed, the hydrogen gas levels may approach threshold T2. If the hydrogen gas level associated with the patient exceeds threshold T2, the artificial feeding system stops delivering nutrient to the patient. This causes the hydrogen gas levels associated with the patient to decrease until the hydrogen gas levels drop below threshold T1. The artificial feeding system then again delivers nutrient to the patient, causing an increase in hydrogen gas concentration associated with the patient.

FIG. 5 illustrates another exemplary method 500 associated with monitoring nutritional uptake based on hydrogen gas concentration associated with a patient. The method 500 can be used to monitor and regulate the continuous feeding of the patient with an artificial feeding system. The method 500 is similar to the method 300 of FIG. 3, except the method 500 adjusts the feeding rates of the artificial feeding system as opposed to the start and stop times associated with the delivery of nutrition to the patient. This ensures that nutrient is continuously delivered to the patient at an ideal feeding rate to prevent malnourishment and overfeeding.

For instance, at 510 a volume of nutrient is delivered to the patient at an initial feeding rate. The volume of nutrient can be delivered by an enteral feeding system. At 520, the hydrogen gas concentration associated with the patient is monitored using a hydrogen gas sensor. For instance, a hydrogen gas sensor can be used to monitor the amount of hydrogen gas in the patient's exhaled breath or in the patient's digestive tract.

At 530, the hydrogen gas concentration is compared to a first threshold value, such as a threshold value in the range of about 5 ppm to about 25 ppm, such as about 10 ppm to about 20 ppm, such as about 20 ppm, or any other hydrogen gas concentration therebetween. If the hydrogen gas concentration is less than first threshold value, the patient is in need of additional nutrition. Accordingly, an alert can be provided to the care giver from an alert system as shown at 540. In addition, the initial feeding rate of the feeding system can be increased to accommodate the patient's need for additional nutrition as shown at 550. A care giver can manually increase the initial feeding rate, or a control loop can automatically adjust feeding system parameters to increase the initial feeding rate delivered to the patient. After increasing the initial feeding rate delivered to the patient, the method 500 returns to 520 and continuously monitors the hydrogen gas associated with the patient to determine if the patient is receiving too little, an ideal amount, or too much nutrition.

At 560, the hydrogen gas concentration is compared to a second threshold, such as a threshold value in the range of about 65 ppm to about 85 ppm, such as about 75 ppm to about 80 ppm, such as about 80 ppm, or any other hydrogen gas concentration therebetween. If the hydrogen gas concentration is less than the second threshold value, but greater than the first threshold, the patient is receiving an ideal an amount of nutrition. Thus, no adjustments to the feeding system are necessary and the method 500 continues to monitor hydrogen gas concentrations associated with the patient.

If the hydrogen gas concentration exceeds the second threshold value, the patient is receiving too much nutrition and is in danger of vomiting or diarrhea. An alert can be provided to the care giver from an alert system as shown at 570. At 580 to prevent overfeeding, the method 500 will decrease the initial feeding rate and will continue to monitor hydrogen gas associated with the patient. When the hydrogen gas level fall below the first threshold, the method 500 will increase the initial feeding rate to prevent the patient from becoming malnourished.

With reference to FIG. 6, an exemplary system 100 for carrying out the methods disclosed above will now be discussed in detail. As illustrated in FIG. 6, the system 100 includes a controller 110, a hydrogen gas sensor 120, a feeding system 130, a user interface 140, and an alert system 150. Feeding system 130 can be any system used to deliver nutrient to a patient, such as an enteral feeding system. For instance, in a particular embodiment, feeding system 130 can include an enteral feeding tube 135 (illustrated in FIG. 7 and FIG. 8) having a distal end inserted into the digestive tract of a patient and a nutrient source. The enteral feeding tube can be inserted into the patient either through the stomach wall of the patient or down the patient's nose or throat. Nutrient is delivered to the patient through enteral feeding tube 135 from the nutrient source at an initial feeding rate controlled by controller 110.

Controller 110 is configured to control feeding system 130 based on signals received from hydrogen gas sensor 120 to ensure that feeding system 130 delivers a proper amount of nutrition to a patient. Controller 110 can be any suitable control device, and can include, for instance, a microcontroller or other control circuitry. User interface 140 can be coupled to controller 110. User interface 140 can be adapted to receive instructions through various peripheral devices from a user. For instance, a user can input commands or other data into user interface 140 through a keyboard, touch-screen, mouse, or other suitable input device. User interface 140 can display data and other information associated with system 100 to a user through a visual display, media element, or other suitable output device.

Controller 110 is coupled to an alert system 150. Controller 110 is configured to control alert system 150 to provide an alert to a care giver based on hydrogen gas levels associated with the patient. For instance, if controller 110 determines that the hydrogen gas level associated with a patient is less than a threshold value, the controller 110 can control alert system 150 to provide an alert to a care giver indicating that the care giver is in need of additional nutrition. The alert can be a visual alert, audible alert, vibratory alert, wireless alert, or other suitable alert.

Hydrogen gas sensor 120 is configured to monitor hydrogen gas levels associated with the patient. Hydrogen gas sensor 120 can be any device that can monitor the hydrogen gas levels generated in a patient's digestive tract as a result of nutritional uptake of the patient.

In a particular embodiment, the hydrogen gas sensor 120 is configured to monitor hydrogen gas in the patient's exhaled breath. The hydrogen gas sensor 120 can be a breathalyzer sensor such as the HBT Sleuth sensor manufactured by Bedford Scientific Ltd. Other suitable sensors include gas chromatography mass spectroscopy (GC-MS) and direct mass spectroscopy sensors that analyze the chemical composition of a collected gas sample. The hydrogen sensor 120 can be a stand-alone breathalyzer sensor that a patient breaths into periodically or can be incorporated as part of a ventilator tube for a patient that is using a ventilator system.

The very small size of certain hydrogen gas sensors can make them suitable for incorporation into an enteral feeding system for monitoring hydrogen gas in a patient's digestive tract. In this regard, the hydrogen gas sensor 120 can be included as part of an enteral feeding system that delivers nutrition to a patient's digestive tract.

For instance, as illustrated in FIG. 7, the hydrogen gas sensor 120 can be included on the distal end of enteral feeding tube 135. As illustrated in FIG. 7, the hydrogen gas sensor 120 is located in the stomach 182 of patient 180. Alternatively, the hydrogen gas sensor 120 could be located in the small intestine 184 of patient 180. The hydrogen gas sensor 120 monitors hydrogen gas levels contained in stomach 182 or small intestine 184 and communicates signals associated with the hydrogen gas levels to controller 110 over communications link 125. Communications link 125 can be a hardwired communication link, such as an optical communication link 125 or other suitable hardwired communication link. Alternatively, hydrogen gas sensor 120 can be configured to communicate wirelessly with controller 120.

Various hydrogen sensors are suitable for use as hydrogen gas sensor 120 located at the distal end of enteral feeding tube 135. For instance, hydrogen gas sensor 120 can be an Optical nose (O-nose) sensor developed by Pranalytica; one of various medical grade sensors manufactured by City Technology, including the model 3HYT, 3MHYT, 4HYT, 7HYE, 7HYT, EZT3HYE, or EZT3HYT sensors; or palladium nanobeads manufactured by Argonne National Laboratories.

Other nanosensors, such as, for example, ZnO nanorod hydrogen sensors developed at University of Florida (Lupan O et al., 2009; "Selective hydrogen gas nanosensors using individual ZnO nanowire with fast response at room temperature," Sensors and Actuators B Chemical); titanium nanotubes developed at Penn State (Varghese O. K., et al., 2003; "Hydrogen sensing using titania nanotubes," Sensors and Actuators, B93, pp 338-344); and/or the nanoflowers (Shafiei M et al., 2010, "Pt/MoO3 nano-flower SiC Schottky diode based hydrogen gas sensors," Prof of IEEE Sensors Conf. 2010, 354-357) could be used as hydrogen gas sensor 120. Oriented graphite nanostructure carbon films that have been employed as a chemiresistive sensor for ultra-sensitive gas sensor applications may also be suitable for hydrogen gas sensor 120 (Rivera I F et. al., 2010; "Graphene based ultra-sensitive gas sensors;" Prof of IEEE Sensors Conf. 2010, 1543-37; Moafi A et al., 2010; "Oriented graphitic carbon films for hydrogen gas sensors," Prof of IEEE Sensors Conf. 2010, 378-381).

As illustrated in FIG. 8, hydrogen gas sensor 120 can alternatively be located on the outside end of enteral feeding tube 120, such as proximate a nutrient source for feeding system 130. The hydrogen gas sensor 120 monitors hydrogen gas levels contained in the digestive tract of the patient and communicates signals associated with the hydrogen gas levels to controller 110 over communications link 125.

Referring to FIG. 9, an exemplary system 400 for monitoring nutritional uptake of an infant is disclosed. The system includes electronic circuitry, such as controller 410 and alert system 430, and a hydrogen gas sensor 420 located as part of a an oral infant device such as a pacifier, bottle or the like device. The hydrogen gas sensor 420 is configured to monitor an amount of hydrogen gas associated with the exhaled breath of the infant. The controller 410 monitors signals received from the hydrogen gas sensor 420 and controls alert system 430 to provide an alert based on the hydrogen gas level detected by the hydrogen gas sensor 420. The alert can be an audible alert, visual alert, vibratory alert, wireless alert, or other suitable alert.

For instance, in a particular embodiment, the hydrogen gas sensor 420 can monitor the amount of hydrogen gas in the exhaled breath of the infant. The controller 410 can receive signals from the hydrogen gas sensor 420 and compare the detected the amount of hydrogen gas with a threshold value. The controller 420 can control the alert system to provide an alert 430 if the amount of hydrogen gas is less than the threshold value. The alert can indicate to a parent or other care giver that the infant is need of additional nutrition and that it is time for feeding.

The exemplary system 400 can be used for instance, by a mother who is breast feeding an infant. A mother that is breast feeding an infant may be unsure whether the infant has received adequate nutrition. To determine if the infant has received adequate nutrition, the mother can monitor the exhaled breath of the infant using a hydrogen gas sensor 420, such as a hydrogen gas sensor incorporated as part of a an oral infant device such as a pacifier, bottle or the like device used by the infant. The hydrogen gas levels can be compared to a threshold value and if the hydrogen gas levels associated with the infant are less than a threshold value, the system 400 can provide an alert through alert system 430 to the mother or other care giver indicating that the baby has not received sufficient nutrition. The mother can then continue breast feeding the infant until the infant has received adequate nutrition.

Example

1. Sensitivity of Hydrogen Gas Sensor

A hydrogen gas sensor was purchased from Bedfont Scientific Inc., Rochester, Kent UK). The system was calibrated using background air (0 ppm hydrogen) and with a sample cylinder containing 100 ppm hydrogen gas (Microdirect Inc., Auburn Me.). The gas stream was allowed to gently blow into the intake of the measure during a reading phase. The sensor measured 100 ppm hydrogen.

2. Monitoring Breath Hydrogen Gas During the Day/Evening in a Human Subject

A healthy male subject (53 yr old) measured his breath hydrogen during the day and evening hours to determine the changes due to feeding. The subject gently inhaled breath, held it for 20 seconds and then gently exhaled through his mouth into the sensor. The results are shown below:

5:30 am—Breath hydrogen measured after fasting since 10 pm the night before; 15 ppm Breakfast at 6:30 am 7 am—Breath hydrogen measured; 48 ppm 11:30 am—Breath hydrogen measured; 20 ppm Lunch at 11:40 am 12 noon—Breath hydrogen measured; 45 ppm 1 pm—Breath hydrogen measured; 55 ppm 6 pm—Breath hydrogen measured; 15 ppm Dinner at 7 pm 8 pm—Breath hydrogen measured; 64 ppm The above results show that breath hydrogen does correlate well to the nutritional uptake of the subject and also to when the subject is feeling hungry.

3. Experiment to Model Feeding Tube with Sensor at Distal End Inside Stomach.

The Perspex model of the stomach and small intestine was used. To the distal end of an enteral feeding tube was attached the hydrogen gas sensor (taped) and this adapted tube was inserted into the stomach via a hole in the stomach wall. A cylinder of 100 ppm hydrogen gas in air was then attached to the bottom of the small intestine tube of the model and a steady stream of gas introduced into the model. A hydrogen gas concentration was then measured by the sensor. The reading was 100 ppm.

4. Experiment Using and Enteral Feeding Tube with Hydrogen Sensor at the Outside of the Tube (Skin Surface at the Stomach)

The hydrogen sensor was mounted on the outside end of the enteral feeding tube where the tube end is on the outside of the stomach on the skin surface. Hydrogen gas at 100 ppm was introduced into the stomach and small intestine via the small intestine tube. The hydrogen gas concentration of the gas exiting the tube was measured by the sensor and was found to be 100 ppm.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A system for monitoring artificial feeding of a patient, the system comprising:
    a feeding device configured to deliver a volume of nutrient to a patient at an initial feeding rate;
    a microflora intestinal gas sensor configured to monitor an amount of microflora intestinal gas associated with the patient; and
    a controller configured to adjust the volume of nutrient delivered to the patient based at least in part on the amount of microflora intestinal gas associated with the patient;
    wherein the feeding device is configured to deliver the volume of nutrient to the patient with both continuous and intermittent delivery separately, and wherein the feeding device is configured to provide nutrient to the patient when the amount of microflora intestinal gas associated with the patient is less than a first threshold value and to stop delivery of nutrient to the patient when the amount of microflora intestinal gas associated with the patient is greater than a second threshold value.

2. The system of claim 1, wherein said feeding device comprises an enteral feeding device having a distal end inserted in said patient and an outside end coupled to a nutrient source.

3. The system of claim 2, wherein said microflora intestinal gas sensor is located at the distal end of said enteral feeding tube.

4. The system of claim 2, wherein said microflora intestinal gas sensor is located at the outside end of said enteral feeding tube.

5. The system of claim 1, wherein said microflora intestinal gas sensor comprises a sensor configured to monitor exhaled breath of the patient.

6. The system of claim 1, wherein said microflora intestinal gas sensor is configured to monitor the amount of microflora intestinal gas in areas selected from the stomach and the small intestine of the patient.

7. The system of claim 1, wherein said system further comprises an alert system configured to provide an alert to a caregiver based at least in part on the amount of microflora intestinal gas monitored by said microflora intestinal gas sensor.

8. The system of claim 1, wherein the system is configured to monitor the amount of microflora intestinal gas associated with the patient before delivering the volume of nutrient to the patient with the feeding device to determine a baseline value of microflora intestinal gas, and wherein the system is configured to determine a relative change in microflora intestinal gas associated with the patient from the baseline value after delivering the volume of nutrient to the patient to adjust the volume of nutrient delivered to the patient based at least in part on the relative change in microflora intestinal gas.

9. The system of claim 1, wherein the feeding device is coupled to a control loop configured to regulate the volume of nutrient delivered by the feeding device based at least in part on the amount of microflora intestinal gas monitored by the microflora intestinal gas sensor.

10. The system of claim 1, wherein the feeding device is configured to increase the initial feeding rate if the monitored amount of microflora intestinal gas is less than a first threshold value, maintain the initial feeding rate substantially constant if the monitored amount of microflora intestinal gas is greater than the first threshold value and less than a second threshold value, and decrease the initial feeding rate if the monitored amount of microflora intestinal gas is greater than the second threshold value.

11. The system of claim 10, wherein the first threshold value is in the range of about 3 ppm to about 25 ppm and the second threshold value is in the range of about 65 ppm to about 85 ppm.

12. The system of claim 1, wherein the microflora intestinal gas sensor is configured to monitor the amount of microflora intestinal gas from areas selected from the patient's breath, the patient's digestive tract, and combinations thereof.

13. The system of claim 1, wherein the microflora intestinal gas is hydrogen.

14. The system of claim 13, wherein monitoring the amount of the microflora intestinal gas associated with the patient includes monitoring a concentration of the microflora intestinal gas associated with the patient.

15. A system for monitoring artificial feeding of a patient, the system comprising:
    a feeding device configured to deliver a volume of nutrient to a patient at an initial feeding rate;
    a microflora intestinal gas sensor configured to monitor an amount of microflora intestinal gas associated with the patient; and
    a controller configured to adjust the volume of nutrient delivered to the patient based at least in part on the amount of microflora intestinal gas associated with the patient;
    wherein the feeding device is configured to provide nutrient to the patient when the amount of microflora intestinal gas associated with the patient is less than a first threshold value and to stop delivery of nutrient to the patient when the amount of microflora intestinal gas associated with the patient is greater than a second threshold value.

16. The system of claim 15, wherein monitoring the amount of the microflora intestinal gas associated with the patient includes monitoring a concentration of the microflora intestinal gas associated with the patient, and wherein the first threshold value is in the range of about 3 ppm to about 25 ppm and the second threshold value is in the range of about 65 ppm to about 85 ppm.

17. The system of claim 15, wherein the microflora intestinal gas is hydrogen.

18. A system for monitoring artificial feeding of a patient, the system comprising:
    a feeding device configured to deliver a volume of nutrient to a patient at an initial feeding rate;
    a microflora intestinal gas sensor configured to monitor an amount of microflora intestinal gas associated with the patient; and
    a controller configured to adjust the volume of nutrient delivered to the patient based at least in part on the amount of microflora intestinal gas associated with the patient;
    wherein the feeding device is configured to increase the initial feeding rate if the monitored amount of microflora intestinal gas is less than a first threshold value, maintain the initial feeding rate substantially constant if the monitored amount of microflora intestinal gas is greater than the first threshold value and less than a second threshold value, and decrease the initial feeding rate if the monitored amount of microflora intestinal gas is greater than the second threshold value.

19. The system of claim 18, wherein monitoring the amount of the microflora intestinal gas associated with the patient includes monitoring a concentration of the microflora intestinal gas associated with the patient, and wherein the first threshold value is in the range of about 3 ppm to about 25 ppm and the second threshold value is in the range of about 65 ppm to about 85 ppm.

20. The system of claim 18, wherein the microflora intestinal gas is hydrogen.

* * * * *